United States Patent
Kinlen et al.

[11] Patent Number: 5,218,304
[45] Date of Patent: Jun. 8, 1993

[54] ELECTRONIC PH AND ORP INDICATOR

[75] Inventors: Patrick J. Kinlen, Fenton; John H. Wagenknecht, Cedar Hill, both of Mo.

[73] Assignee: Monsanto Company, St. Louis, Mo.

[21] Appl. No.: 846,504

[22] Filed: Mar. 6, 1992

[51] Int. Cl.[5] .................. G01N 27/27; G01N 27/416
[52] U.S. Cl. .................................. 324/438; 324/71.1; 324/450; 204/433; 204/412
[58] Field of Search .................. 324/438, 71.1, 439, 324/444, 446, 450; 204/411, 412, 433, 153.21

[56] References Cited

U.S. PATENT DOCUMENTS

| | | | |
|---|---|---|---|
| 3,726,777 | 4/1973 | Macur | 204/433 X |
| 3,959,087 | 5/1976 | Morrow | 204/1 T |
| 4,028,197 | 6/1977 | Capuano | 204/1 T |
| 4,033,871 | 7/1977 | Wall | 210/96 R |
| 4,090,925 | 5/1978 | Jungman | 204/433 X |
| 4,176,031 | 11/1979 | Rosenblum | 204/195 R |
| 4,224,154 | 9/1980 | Steininger | 210/85 |
| 4,338,175 | 7/1982 | Binder et al. | 324/438 X |
| 4,442,405 | 4/1984 | Andrejasich et al. | 324/439 |
| 4,657,670 | 4/1987 | Newton | 210/85 |
| 4,801,886 | 1/1989 | Steininger | 324/438 |
| 4,825,207 | 4/1989 | Snell | 340/825.17 |
| 4,940,946 | 7/1990 | Nazaryan | 324/438 |
| 5,103,179 | 4/1992 | Thomas et al. | 324/438 |

FOREIGN PATENT DOCUMENTS

| | | |
|---|---|---|
| 8434226 | 4/1985 | Australia . |
| 2719015 | 11/1978 | Fed. Rep. of Germany . |
| 2830313 | 1/1980 | Fed. Rep. of Germany . |
| 3004494 | 8/1981 | Fed. Rep. of Germany . |
| 2492531 | 4/1982 | France . |

OTHER PUBLICATIONS

Strantrol Operation/Maintenance Manual For Model 720 1991 Stranco, Ltd. Rev. May 1991. 700-20-MF86.
Canelli, Edmondo "Evaluation of A Portable Bare--Electrode Amperometic Analyzer For Determining Free Chlorine In Potable And Swimming-Pool Water" Water Res., 14(10), 1533-40; 1980, Dec. Abstract.
Hu, Hua-Ching, "Chronoamperometric Determination of Free Chlorine By Using A Wax-Impregnated Carbon-Electrode", J-Am Water Works Assoc., 73(3), 150-3; 1981, Dec. (Abstract).

Primary Examiner—Jack B. Harvey
Attorney, Agent, or Firm—Lawrence L. Limpus

[57] ABSTRACT

A sensor which may be immersed in a fluid to measure the pH and the ORP potential of the fluid is taught. The sensor has three solid state electrodes, a pH sensing electrode, a reference electrode and an ORP potential sensing electrode, which extend from a fluid-tight enclosure. The enclosure further contains a display means for indicating the pH measurement and the ORP potential measurement.

20 Claims, 2 Drawing Sheets

ELECTRONIC PH AND ORP INDICATOR

BACKGROUND OF THE INVENTION

This invention relates to a sensor which may be used over an extended period of time in a fluid to indicate the pH and the oxidation-reduction potential (ORP) of the fluid.

More particularly, this invention relates to a sensor which can remain in water for an extended period of time to continuously indicate the pH and the oxidation-reduction potential (ORP) of the water.

More particularly, this invention relates to a sensor which can be immersed in swimming pools, or other bodies of water which contain chlorine, for an extended period of time to continuously indicate the pH and chlorine content of the water.

DESCRIPTION OF THE PRIOR ART

Bodies of treated water are required for many purposes in industry, recreation and education and for each user the problems encountered in maintaining the quality of the water require great efforts. Typically the efforts of industry to maintain cooling tower and process water and the efforts of governments and individuals to maintain many other bodies of water such as, for example, drinking water supplies, swimming pools and aquariums require constant attention to the water conditions and, in particular, to the pH of the water and to the amount of chlorine that is present. These measurements must be taken frequently and the results are often inaccurate.

Similar problems are encountered by the users and producers of many other fluids such as oils, organic resins and food products such as juices and other food products containing liquids. Producers of fruit juices, for example, are concerned about the pH of their product and about the amount of ascorbic acid that is present. Numerous materials can create an ORP potential in a fluid and examples of these materials are chlorine, bromine and permanganates which are oxidizing agents and ascorbic acid, formaldehyde and hydrazine which are reducing agents. Measurement and control of these and other similar materials are of concern in many processes.

The problems often encountered in the control of the pH and ORP potentials of a fluid may be shown by an example. A common method for measuring the pH of a body of water such as that found in a swimming pool requires daily sampling using wet chemistry in which a sample of the water being tested is mixed with an indicator fluid and the color of the resultant mixture is compared to the colors shown on a chart to determine the pH of the water. This process is often inconvenient, especially for a homeowner with a swimming pool, and it often provides incorrect readings of the pH of the water. The measurement of the sample of water and of the indicator fluid is often inexact and, as a result, the color of the mixture varies. Furthermore, the visual comparison of the color of the mixture with the colors shown on the chart is also inexact. Thus, the measured pH may vary a great deal from the actual pH of the water and any treatment of the water based upon that measurement may not be correct.

SUMMARY OF THE INVENTION

This invention is directed to a sensor which will remain for an extended period of time in a fluid, such as a body of water to continuously measure and indicate the pH and the oxidation-reduction (ORP) potential of the fluid. The sensor may also be called an indicator, or other similar names, and these names are considered to be equivalent.

The invention is a sensor which may be immersed in a fluid to measure the pH and the ORP potential of the fluid. The sensor, which will be within a fluid-tight enclosure, has three solid state electrodes which extend into the fluid. The first electrode is a pH sensing electrode, the second is a reference electrode for the first and third electrodes and the third is an ORP potential sensing electrode. The enclosure further contains a display means visible from outside the enclosure for indicating the pH measurement and the ORP potential.

These and other features and advantages of the present invention will become apparent from the following detailed description, wherein reference is made to the figures in the accompanying drawings.

DESCRIPTION OF THE PREFERRED EMBODIMENTS

Figure 1:
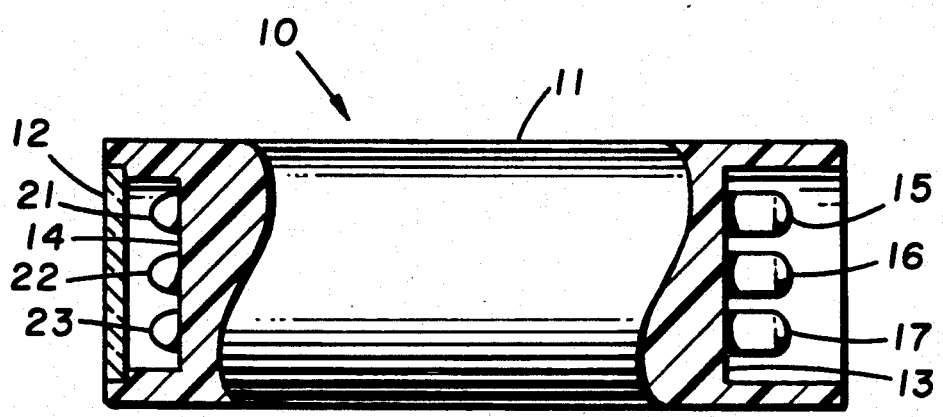
FIG. 1 is a side view of a sealed enclosure that houses the sensor showing the position of the electrodes and the display means.
Figure 2:
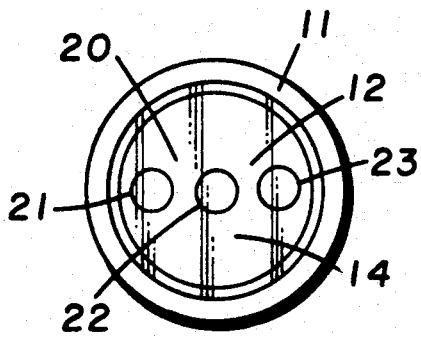
FIG. 2 is a view of the face of the enclosure showing the display means.
Figure 3:
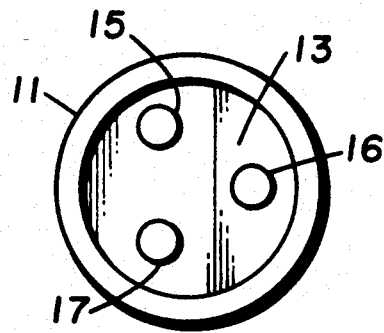
FIG. 3 is a view of the back of the enclosure showing electrodes which extend from the enclosure into the fluid.

FIGS. 1 through 4 show the invention which is a sensor 10 which will remain immersed for an extended period of time in a fluid containing a material whose presence creates an oxidation-reduction (ORP) potential in the fluid to continuously indicate the pH and the OR potential of the fluid. The fluid may be water for any use such as, for example, industrial cooling and process water, drinking water, and water for swimming pools, aquariums and spas. The fluid may also be a food product such as, for example, juices, cheeses and other food products containing liquids, or cooking and lubricating oils, organic resins or other liquids in manufacturing processes and food preparation. However, it is contemplated that the sensor 10 will be most useful in swimming pools, spas, aquariums, cooling towers and other similar bodies of water in which the measurement of the pH and the chlorine content must be routinely and repetitively performed.

The description of the use of the sensor in swimming pools hereinafter is not meant to limit the applicability of the sensor for use in other applications such as spas, cooling towers and aquariums, nor is it meant to limit the applicability of the sensor for use in fluids other than water.

The sensor 10 has a fluid- or water-tight, sealed enclosure 11 that is preferably immersed in, but may be allowed to float on, the fluid to provide a continuous indication of the pH and the oxidation-reduction (ORP) potential of the fluid. The sensor 10 has three solid state electrodes which extend into the fluid. The first electrode 15 is a solid state junction-type metal/metal oxide pH sensing electrode which may be, for example, an iridium-iridium oxide electrode such as the electrode described in U.S. Pat. No. 4,818,365, the specification of which is incorporated by reference. The second electrode 16 is a solid state junction-type metal/metal salt reference electrode which may be, for example, a silver-silver chloride electrode such as the electrode described in U.S. Pat. No. 4,908,117, the specification of which is incorporated by reference. The third electrode 17 is an electrode for measuring the oxidation-reduction (ORP) potential of the fluid. It is preferred that the third electrode 17 be a platinum electrode; however, the electrode may alternatively be made of other similar materials such as gold and palladium. If electrode 17 is platinum, it may be a platinum wire but it preferably may be produced, for example, by sputtering platinum on a nonconductive substrate, such as ceramic, or on a thin polyester film, such as Mylar ® produced by E. I. duPont de Nemoirs and Company. The second electrode 16 serves as the reference electrode for both the pH measurement and the ORP potential measurement. It is contemplated that the first and second electrodes, 15 and 16, can be coated with a perfluorocarbon coating such as the Nafion ® polymer made by the E. I. duPont de Nemoirs and Company.

If the three solid state electrodes are produced in accordance with the patents described above, then the electrodes will extend through one surface, or wall, 13 of the enclosure 11, as shown in FIG. 1, so that the electrodes are in contact with the fluid. The electrodes pass through seals (not shown), such as o-ring seals or other commonly known seals, in the surface 13 which prevent the fluid from entering the water-tight, sealed enclosure 11.

It is also contemplated that the electrodes may be produced in a manner different from that described above. The electrodes may, for example, be produced as coatings on the surface of a conductive material embedded in a nonconductive substrate as described in pending U.S. patent application Ser. No. 07/450,783, filed Dec. 14, 1989, the specification of which is incorporated by reference. If the electrodes are produced in this manner, the nonconductive substrate, instead of the electrodes as described above, would extend through surface 13 of enclosure 11 to provide contact between the electrodes and the fluid. Alternatively, the nonconductive substrate may be attached to the exterior of the enclosure 11 by adhesives, or any other commonly known method, and wires from the electrodes to the sensor electronics would extend through a seal in the surface 13 of enclosure 11.

Figure 4:
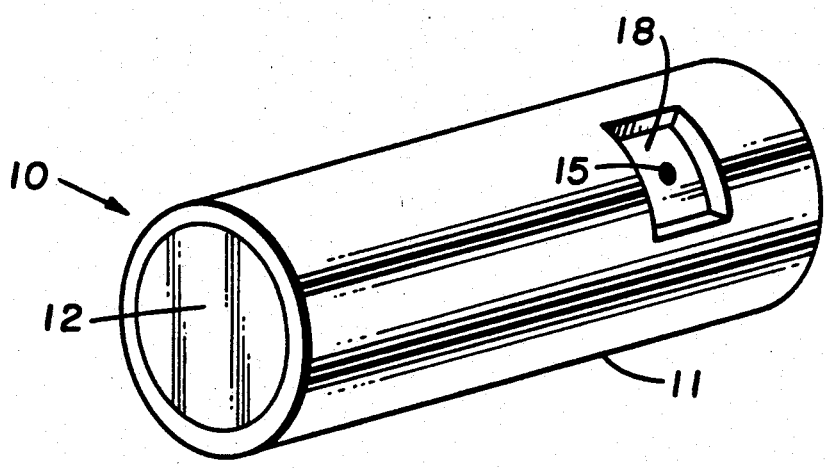
FIG. 4 is a view of a portion of the enclosure surface showing an alternate position for the electrodes.

The electrodes may also be produced by coating the appropriate material on thin substrates such as films. For electrodes produced on thin films, the enclosure 11 may be modified as shown in FIG. 4 to provide one or more apertures or windows 18 in the sides of the enclosure so that the electrodes may be mounted within the enclosure 11 while maintaining contact with the fluid. The thin substrate supporting the electrodes is mounted within the enclosure 11 with the electrodes centered within the opening of the aperture 18 and facing outward from the enclosure. Each electrode may be positioned within a separate aperture 18 or the three electrodes may be centered within a single aperture 18. The surface between the aperture or the inner wall of the enclosure 11 surrounding the aperture 18 and the surface of the substrate supporting the electrodes is sealed using any commonly known method such as a gasket or adhesive.

The sensor 10 also includes display means 20, visible from the exterior of the enclosure 11, for indicating that the pH of the fluid is within the desired range and that there is a sufficient ORP potential present in the fluid. The display means 20 is mounted on an interior surface 14 of enclosure 11 and is visible from the exterior of the enclosure 11 through the transparent panel or window 12. The display means 20 may be any appropriate indicator such as lights, meters or liquid crystal displays that will provide a visual display of the measured values. While meters are easily read, it is preferred that the display means 20 be indicator lights such as colored light emitting diodes (LED) which are easily seen but require very little electrical power to operate. As an example, display means 20 includes a first light, a green light, 21 which flashes if the measured pH level is too low, a second light, a red light, 22 which flashes if the measured pH level is too high, and a third light, a yellow light, 23 that flashes if the measured ORP potential is too low. The red light 22 is also used to indicate that the sensor is operating properly. If the sensor malfunctions, the red light 22 glows steadily. It is also desired to provide an indication of how much the measured values for the pH and ORP potential of the fluid deviate from the desired levels. To provide this indication, the flashing of the lights is varied with the flashing becoming more rapid as the measured value deviates farther from the desired levels.

Power for the sensor is provided by batteries within the enclosure 11. The power required, and the size of the battery, depends upon the design of the electrical circuit, the desired operational life of the sensor before the battery must be replaced, and the space available within the enclosure for the battery. For this sensor, six volts are provided by four expendable AA size dry cell batteries. Optionally, a light may be provided or one of the lights of the display means may be used to indicate that battery power for the sensor is getting low, that is, that the batteries are becoming discharged and that they should be replaced to maintain the proper operation of the sensor.

Figure 5:
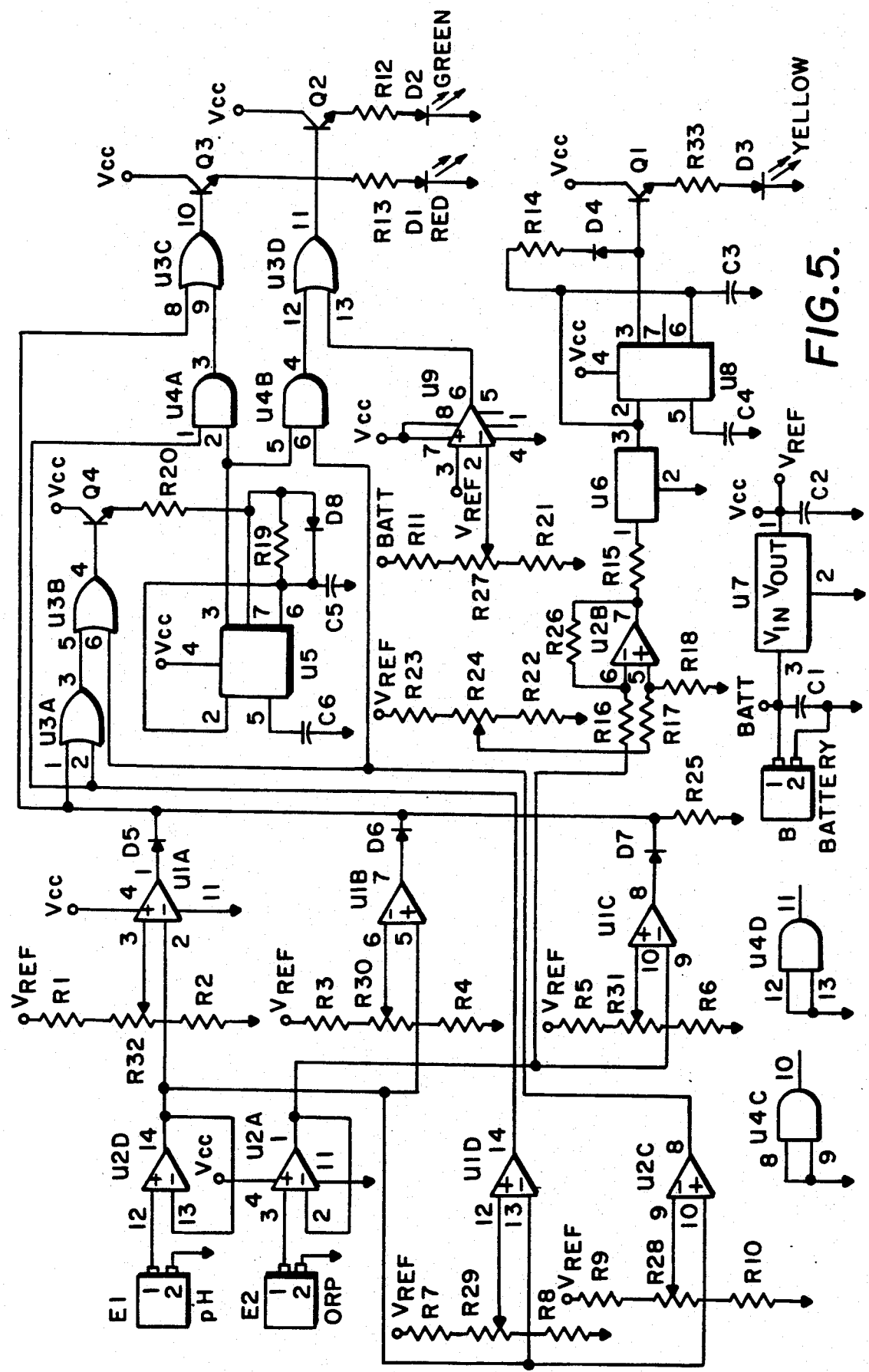
FIG. 5 is a circuit diagram illustrating an electrical circuit for the sensor.

FIG. 5 is an electrical circuit diagram for the sensor of this invention. The integrated circuit devices used in the circuit and the other circuit elements are identified in Table 1. In Table 1 the values of the resistors are shown in ohms, with "M" indicating megohms and "K" indicating kilo-ohms, and the value of the capacitors is shown in microfarads. While this is the circuit used with this invention, it is recognized that other circuits may be designed and that the other circuits may perform the same function equally well.

TABLE 1

| LABEL | DESCRIPTION | VALUE | MANUFACTURER |
|---|---|---|---|
| R1 | Resistor | 2.2M | |
| R2 | Resistor | 24K | |
| R3 | Resistor | 2.2M | |
| R4 | Resistor | 100K | |
| R5 | Resistor | 2.2M | |
| R6 | Resistor | 150K | |
| R7 | Resistor | 1.2M | |
| R8 | Resistor | 22K | |
| R9 | Resistor | 1.2M | |
| R10 | Resistor | 33K | |
| R11 | Resistor | 220K | |
| R12 | Resistor | 1K | |
| R13 | Resistor | 1K | |

TABLE 1-continued

| LABEL | DESCRIPTION | VALUE | MANU-FACTURER |
|---|---|---|---|
| R14 | Resistor | 47K | |
| R15 | Resistor | 470K | |
| R16 | Resistor | 1K | |
| R17 | Resistor | 1.8M | |
| R18 | Resistor | 3.6M | |
| R19 | Resistor | 1M | |
| R20 | Resistor | 270K | |
| R21 | Resistor | 3.3M | |
| R22 | Resistor | 680K | |
| R23 | Resistor | 3.3M | |
| R24 | Potentiometer | 1M | |
| R25 | Resistor | 4.7M | |
| R26 | Resistor | 100K | |
| R27 | Potentiometer | 1M | |
| R28 | Potentiometer | 200K | |
| R29 | Potentiometer | 200K | |
| R30 | Potentiometer | 500K | |
| R31 | Potentiometer | 100K | |
| R32 | Potentiometer | 50K | |
| R33 | Resistor | 1K | |
| C1 | Capacitor | 0.1 μF | |
| C2 | Capacitor | 10 μF | |
| C3 | Capacitor | 1 μF | |
| C4 | Capacitor | 0.01 μF | |
| C5 | Capacitor | 1 μF | |
| C6 | Capacitor | 0.01 μF | |
| D1 | Light Emitting diode - Red | | |
| D2 | Light Emitting Diode Green | | |
| D3 | Light Emitting Diode Yellow | | |
| D4 | Diode | IN 4001 | |
| D5 | Diode | IN 4001 | |
| D6 | Diode | IN 4001 | |
| D7 | Diode | IN 4001 | |
| D8 | Diode | IN 4001 | |
| Q1 | Transistor | PN 2222A | |
| Q2 | Transistor | PN 2222A | |
| Q3 | Transistor | PN 2222A | |
| Q4 | Transistor | PN 2222A | |
| U1 | Integrated Circuit | TLC274ACN/P | Texas Instrument |
| U2 | Integrated Circuit | TLC274ACN/P | Texas Instrument |
| U3 | Integrated Circuit | CD4071BE | Harris |
| U4 | Integrated Circuit | CD4081BE | Harris |
| U5 | Integrated Circuit | TLC555CN/P | National Semiconductor |
| U6 | Integrated Circuit | TL011CLP | Texas Instruments |
| U7 | Integrated Circuit | LM2931-5AQ | Motorolla |
| U8 | Integrated Circuit | TLC555CN/P | National Semiconductor |
| U9 | Integrated Circuit | LM741/P | Signetics |
| E1 | pH Sensing Electrode | | |
| E2 | ORP Sensing Electrode | | |
| Ground | Reference Electrode | | |
| B | Battery | | |

Normally, it is presumed that maintaining a free-chlorine residual of two milligrams per liter or two parts per million, provides good water quality. Within the past few years, the National Environmental Health Association and the National Sanitation Foundation have indicated that the measurement of the oxidation-reduction potential (ORP) is more important because it will distinguish between free and combined chlorine. ORP is defined as the oxidation-reduction potential of a sanitizer such as chlorine. These oxidizers "burn-off" impurities in the water, including body wastes, algae and bacteria. An ORP sensor measures the potential generated by the active form of the sanitizer, and not the inactive forms such as combined chlorine. ORP testing is an ongoing electronic process that monitors sanitation levels. It has been determined that the free chlorine levels are more than adequate if the ORP measurement at platinum is at an acceptable level of approximately 650 millivolts or greater relative to a silver-silver chloride reference electrode, depending upon the pH of the fluid. The third electrode 17, discussed above regarding the measurement of the amount of chlorine in the water, is actually measuring the oxidation-reduction potential of the free-chlorine in the water. The yellow light 23 flashes whenever the measured potential is less than approximately 650 millivolts, relative to the silver-silver chloride reference electrode, to indicate that additional chlorine should be added to the water.

For a swimming pool the sensor 10 is in a sealed, water-tight enclosure 11 from which three electrodes extend. The electrodes are a solid state iridium-iridium oxide electrode 15 for the measurement of pH, a platinum electrode 17 for the measurement of the amount of chlorine present and a solid state silver-silver chloride reference electrode 16 that functions as a reference electrode for both of the measurement electrodes. The enclosure 11 includes a transparent panel or window 12 through which the indicator lights, colored light emitting diodes, that form display means 20 may be seen. Display means 20 includes a first light, a green light, 21 which flashes if the measured pH level is lower than the desired minimum of 7.0 pH, a second light, a red light, 22 which flashes if the measured pH level is higher than the desired maximum of 8.0 pH, and a third light, a yellow light, 23 that flashes if the measured chlorine level is lower than the desired minimum of 1 to 2 parts per million of chlorine in the water. Thus the appropriate light will flash a warning when the measured pH of the water is outside the desired range of 7.0-8.0 pH and when the chlorine content of the water is less than the safe minimum. If the sensor 10 is not functioning properly, the red light 22 will operate continuously, that is it will glow steadily instead of flashing, to provide a warning of the malfunction of the sensor 10.

The sensor has been described as being self-contained within a sealed enclosure. However, it is also possible to separate the electrodes from the electrical circuit and the display means to provide a display of the pH and ORP measurement at a location remote from the fluid. For this configuration, the electrodes are mounted in a sealed enclosure, such as the enclosure described above for the sensor, which can be immersed so that the electrodes are in contact with the fluid. The electrodes and the enclosure may be produced as described above. The electrical circuit and the display means, which are also produced as described above, are contained within a second enclosure that may be mounted at any convenient location and an electrical cable, with the necessary number of wires, is used to connect the electrodes to the electrical circuit. Since this configuration moves the electrical circuit and the display means to a location remote from the fluid, it is possible to replace the batteries that provide power for the sensor with another source of power. With a small change to the electrical circuit, it is possible to use a direct current source or an alternating current source to provide power for the sensor.

It will be apparent from the foregoing that many other variations and modifications may be made in the apparatus and methods herein before described, by those having experience in this technology, without departing from the concept of the present invention. Accordingly, it should be clearly understood that the apparatus and methods depicted in the accompanying drawings and referred to in the foregoing description are illustrative only and not intended to have limitations on the scope of the invention.

We claim:

1. A sensor for measuring the pH and the oxidation-reduction potential of a fluid comprising a first, a second and a third solid state electrode, said first electrode being a pH sensing electrode, said second electrode being a reference electrode for said first and third electrodes and said third electrode being an oxidation-reduction potential sensing electrode, said electrodes extending from a fluid-tight enclosure having display means for indicating said pH and oxidation-reduction potential measurement.

2. The sensor of claim 1 wherein said first electrode is a solid state metal/metal oxide pH sensing electrode and said second electrode is a solid state metal/metal salt reference electrode.

3. The sensor of claim 2 wherein said first electrode is a solid state iridium/iridium oxide pH measurement electrode and said second electrode is a solid state silver/silver chloride reference electrode.

4. The sensor of claim 3 wherein said first and said second electrodes are coated with a perfluorocarbon polymer coating.

5. The sensor of claim 1 wherein said third electrode is a platinum electrode for measuring the oxidation-reduction potential of said fluid.

6. The sensor of claim 1 wherein said display means comprises a first light for indicating low pH, a second light for indicating high pH, and a third light for indicating low oxidation-reduction potential.

7. The sensor of claim 1 wherein said display means comprises a meter for indicating said pH measurement and a light for indicating said oxidation-reduction potential measurement.

8. The sensor of claim 1 wherein said display means comprises a liquid crystal display.

9. The sensor of claim 1 wherein said fluid-tight enclosure floats on the surface of said fluid.

10. The sensor of claim 1 wherein said fluid-tight enclosure is immersed in said fluid.

11. A sensor for measuring the pH and the chlorine content of a body of water comprising a first, a second and a third solid state electrode, said first electrode being a pH sensing electrode, said second electrode being a reference electrode for said first and third electrodes and said third electrode being a chlorine sensing electrode, said electrodes extending from a water-tight enclosure having display means for indicating said pH and chlorine measurement.

12. The sensor of claim 11 wherein said first electrode is a solid state metal/metal oxide pH sensing electrode and said second electrode is a solid state metal/metal salt reference electrode.

13. The sensor of claim 12 wherein said first electrode is a solid state iridium/iridium oxide pH measurement electrode and said second electrode is a solid state silver/silver chloride reference electrode.

14. The sensor of claim 13 wherein said first and said second electrodes are coated with a perfluorocarbon polymer coating.

15. The sensor of claim 11 wherein said third electrode is a platinum electrode for measuring the amount of chlorine present in the water.

16. The sensor of claim 11 wherein said display means comprises a first light for indicating low pH, a second light for indicating high pH, and a third light for indicating low chlorine content.

17. The sensor of claim 11 wherein said display means comprises a meter for indicating said pH measurement and a light for indicating said chlorine measurement.

18. The sensor of claim 11 wherein said display means comprises a liquid crystal display.

19. The sensor of claim 11 wherein said water-tight enclosure floats on the surface of said water.

20. The sensor of claim 11 wherein said water-tight enclosure is immersed in said water.

* * * * *